United States Patent
Russo et al.

(10) Patent No.: US 6,849,050 B1
(45) Date of Patent: Feb. 1, 2005

(54) SYSTEM AND METHOD FOR DETERMINING VISUAL ALERTNESS

(75) Inventors: Michael B. Russo, Sandy Spring, MD (US); Saul Santiago, Columbus, NJ (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 199 days.

(21) Appl. No.: 10/136,625

(22) Filed: Apr. 29, 2002

Related U.S. Application Data

(60) Provisional application No. 60/288,925, filed on May 7, 2001.

(51) Int. Cl.[7] ............................................. A61B 13/00
(52) U.S. Cl. .................................................... 600/558
(58) Field of Search ....................... 600/558; 340/573.1, 340/575, 576; 351/200, 222, 224, 237; 180/272

(56) References Cited

U.S. PATENT DOCUMENTS

| | | | | |
|---|---|---|---|---|
| 3,975,708 A | * | 8/1976 | Lusk et al. | 340/458 |
| 5,219,322 A | * | 6/1993 | Weathers | 600/27 |
| 5,392,030 A | * | 2/1995 | Adams | 340/576 |
| 6,575,902 B1 | * | 6/2003 | Burton | 600/558 |
| 6,650,251 B2 | * | 11/2003 | Gerrity | 600/558 |

* cited by examiner

Primary Examiner—Eric F. Winakur
(74) Attorney, Agent, or Firm—Elizabeth Arwine

(57) ABSTRACT

In one embodiment, a method is characterized by presenting a first pattern of light during a first interval of time: recording a first-pattern response set; presenting a second pattern of light during a second interval of time; recording a second-pattern response set; and assessing visual alertness in response to the first-pattern response set and the second-pattern response set. In one embodiment, a related system includes but is not limited to circuitry and/or programming for effecting the foregoing-referenced method embodiment; the circuitry and/or programming can be virtually any combination of hardware, software, and/or firmware configured to effect the foregoing-referenced method embodiment depending upon the design choices of the system designer.

46 Claims, 11 Drawing Sheets

SYSTEM AND METHOD FOR DETERMINING VISUAL ALERTNESS

CROSS-REFERENCE TO RELATED APPLICATION

This application claims the benefit of U.S. Provisional Patent Application No. 60/288,925 filed May 7, 2001, naming Michael B. Russo and Saul Santiago as inventors, said provisional application hereby incorporated by reference herein in its entirety.

STATEMENT REGARDING FEDERALLY SPONSORED RESEARCH OR DEVELOPMENT

The government has certain rights in this invention.

BACKGROUND OF THE INVENTION

1. Field of the Invention

The present application relates, in general, to sleep deprivation.

2. Description of the Related Art

Human beings require a certain minimum amount and/or regularity of sleep to function effectively. Exactly how much sleep an individual needs, and how regularly such sleep should be taken, varies from person to person. However, each individual does tend to have certain minimal sleep requirements, and it is well known in the art that if an individual is deprived of his minimal sleep requirements, at some point the individual will suffer measurable degradation in either or both his mental and physical functioning.

An individual's mental and/or physical degradation that results from sleep deprivation can be severe. For example, recent studies have shown that significantly sleep deprived individuals exhibit the same amount of impairment as legally intoxicated individuals.

Many professions require that individuals go without sleep for extended periods of time and/or engage in highly erratic sleep patterns. For example, long-haul truck drivers and oilfield workers routinely perform their jobs for periods of 18, 24, 36, or 48 hours. As another example, factory workers are often routinely rotated between day shift and night shift, which interrupts such workers' ordinary and normal sleep patterns. As yet another example, military pilots are often called upon to both fly for extended periods without sleep and engage in sleep at very erratic intervals, especially during wartime operations. Those having ordinary skill in the art will recognize that many other examples are possible.

All of the foregoing examples result in sleep deprivation of some type (e.g., either by a deprivation of the amount or required rhythm of sleep). Furthermore, in all of the foregoing examples, the potential consequences associated with sleep deprivation impairment can prove disastrous in terms of truck or automobile accidents, on the job injuries, aircraft accidents, and/or "friendly fire" incidents. This is especially true in light of the relatively recent findings that physical and/or mental impairments resulting from sleep deprivation can prove as bad or worse than significant alcohol induced intoxication.

In light of the foregoing, it is apparent that a need exists for processes and systems which provide for the detection of physical and/or mental impairment arising from sleep deprivation.

BRIEF SUMMARY OF THE INVENTION

The inventors named herein (the "inventors") have devised a process and related system which provide for the detection of physical and/or mental impairment arising from sleep deprivation.

In one embodiment, a method is characterized by presenting a first pattern of light during a first interval of time; recording a first-pattern response set; presenting a second pattern of light during a second interval of time; recording a second-pattern response set; and assessing visual alertness in response to the first-pattern response set and the second-pattern response set.

In one embodiment, a related system includes but is not limited to circuitry and/or programming for effecting the foregoing-referenced method embodiment; the circuitry and/or programming can be virtually any combination of hardware, software, and/or firmware configured to effect the foregoing-referenced method embodiment depending upon the design choices of the system designer.

In one embodiment, an apparatus is characterized by a Lateral Visual Field Testing Device having at least one light spaced at least one degree relative to a midsagittal plane of a pre-defined test subject position.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

Figure 3:
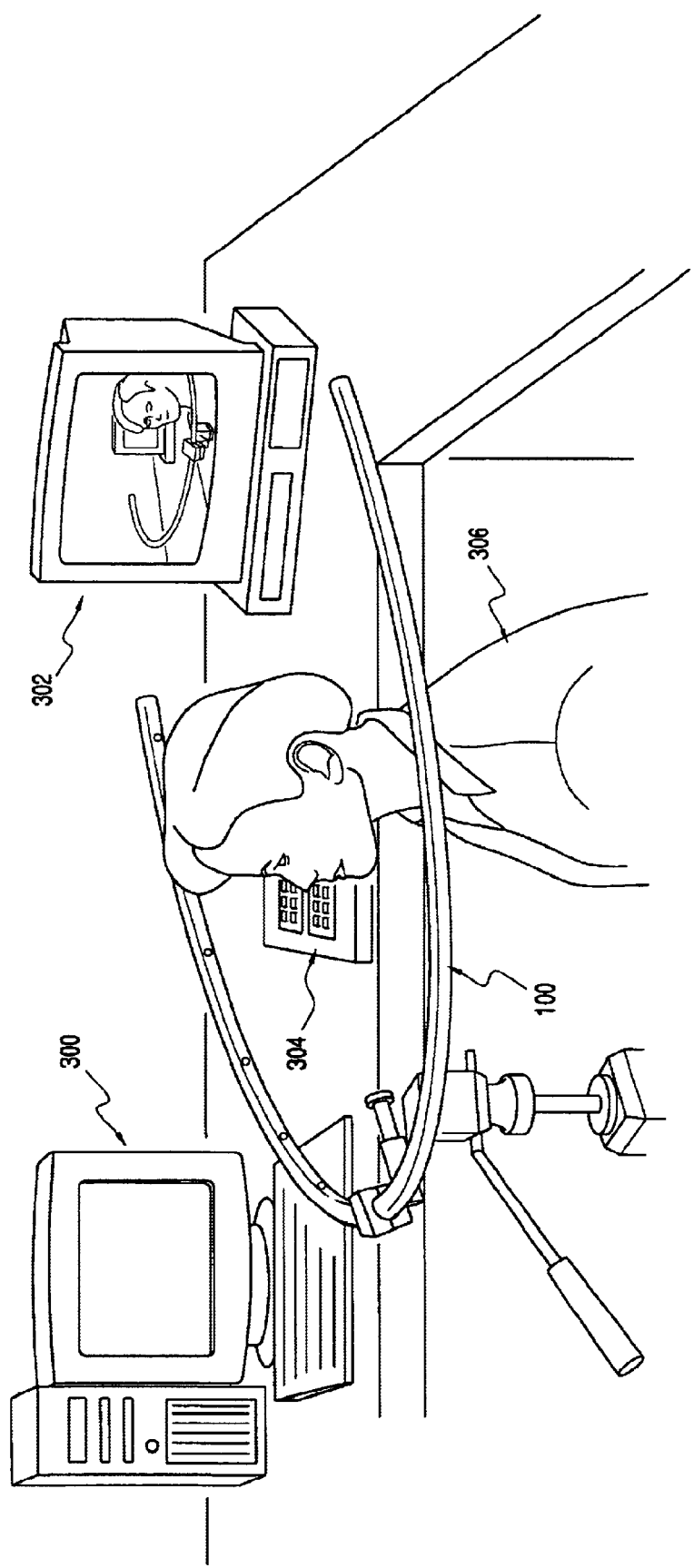

FIG. 3 shows a perspective view of an implementation of the LVFT device 100 in the context of a data processing system 300, audio-visual recording machinery 302, and an interface device 304.

Figure 4:
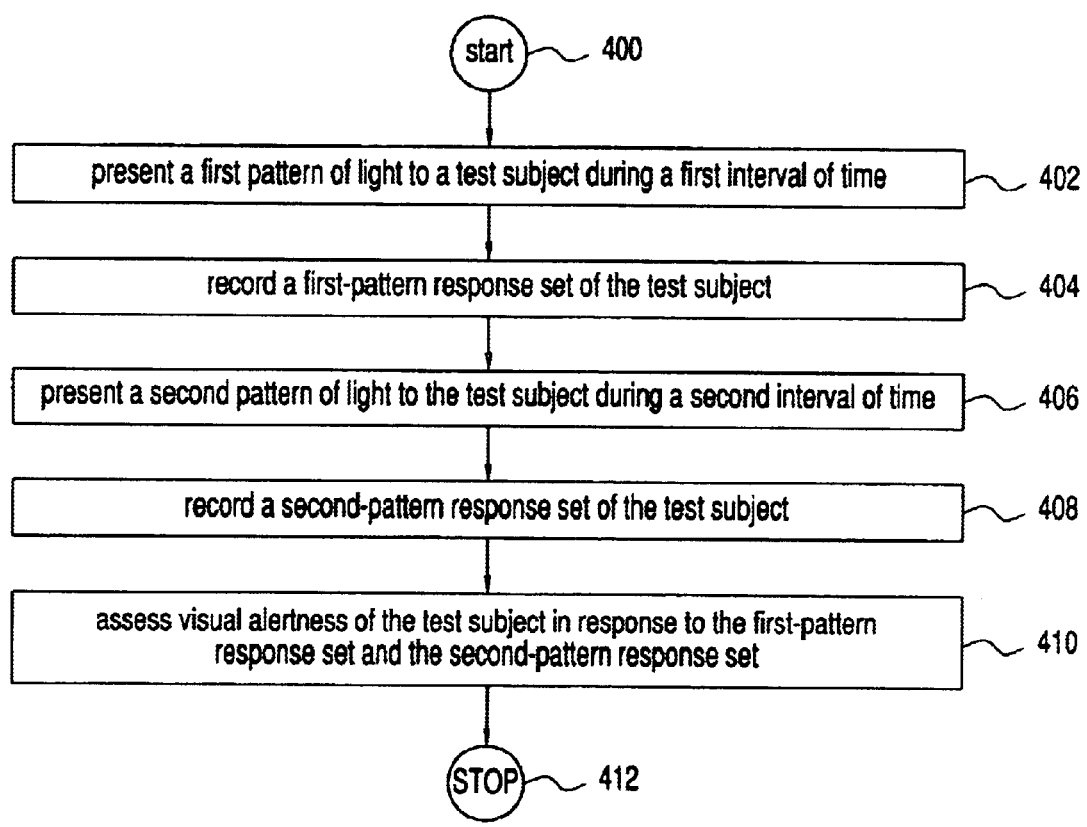

FIG. 4 shows a high-level logic flowchart depicting a process.

Figure 5:
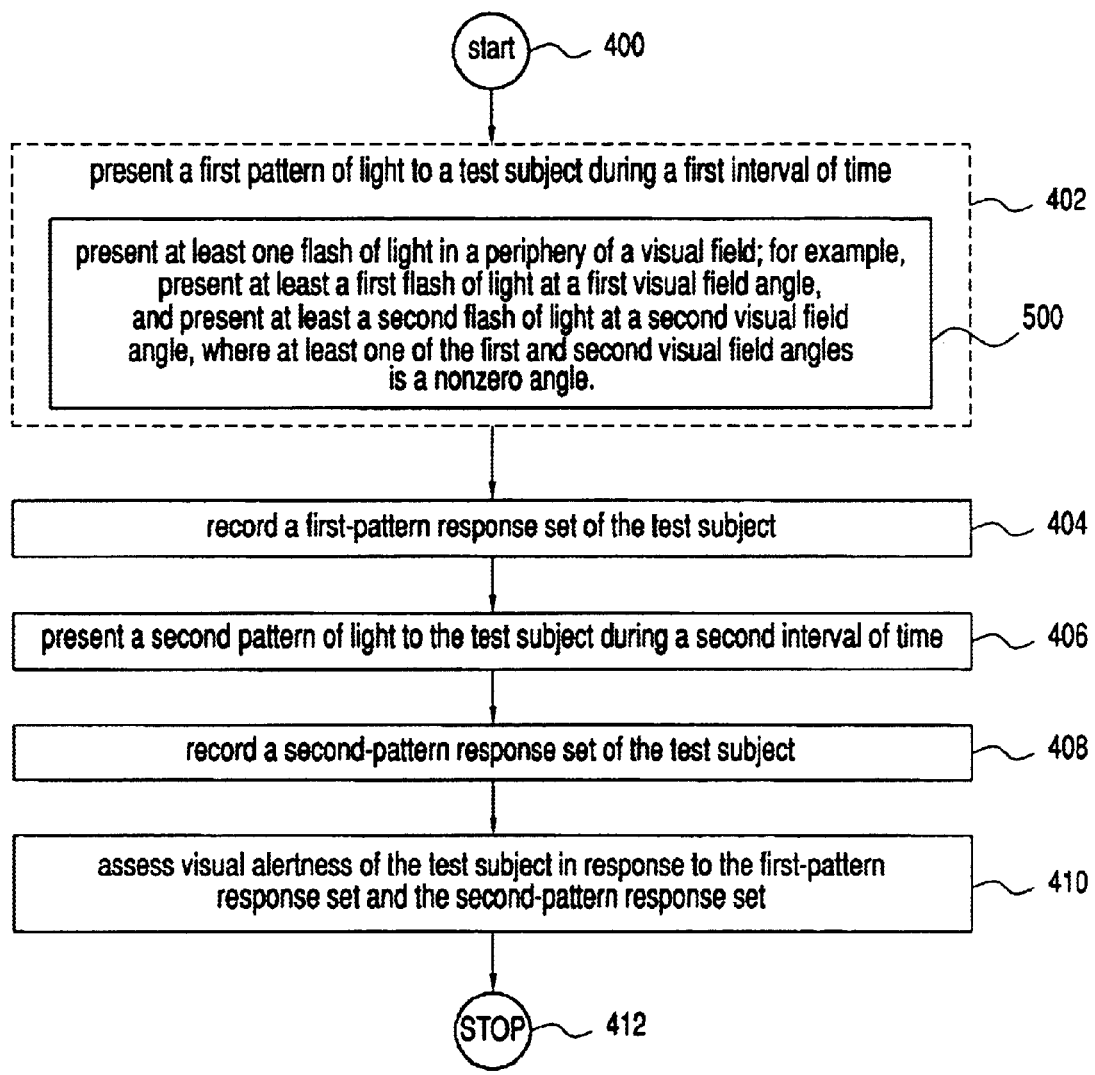

FIG. 5 shows an alternate implementation of the process depicted in FIG. 4.

Figure 6:
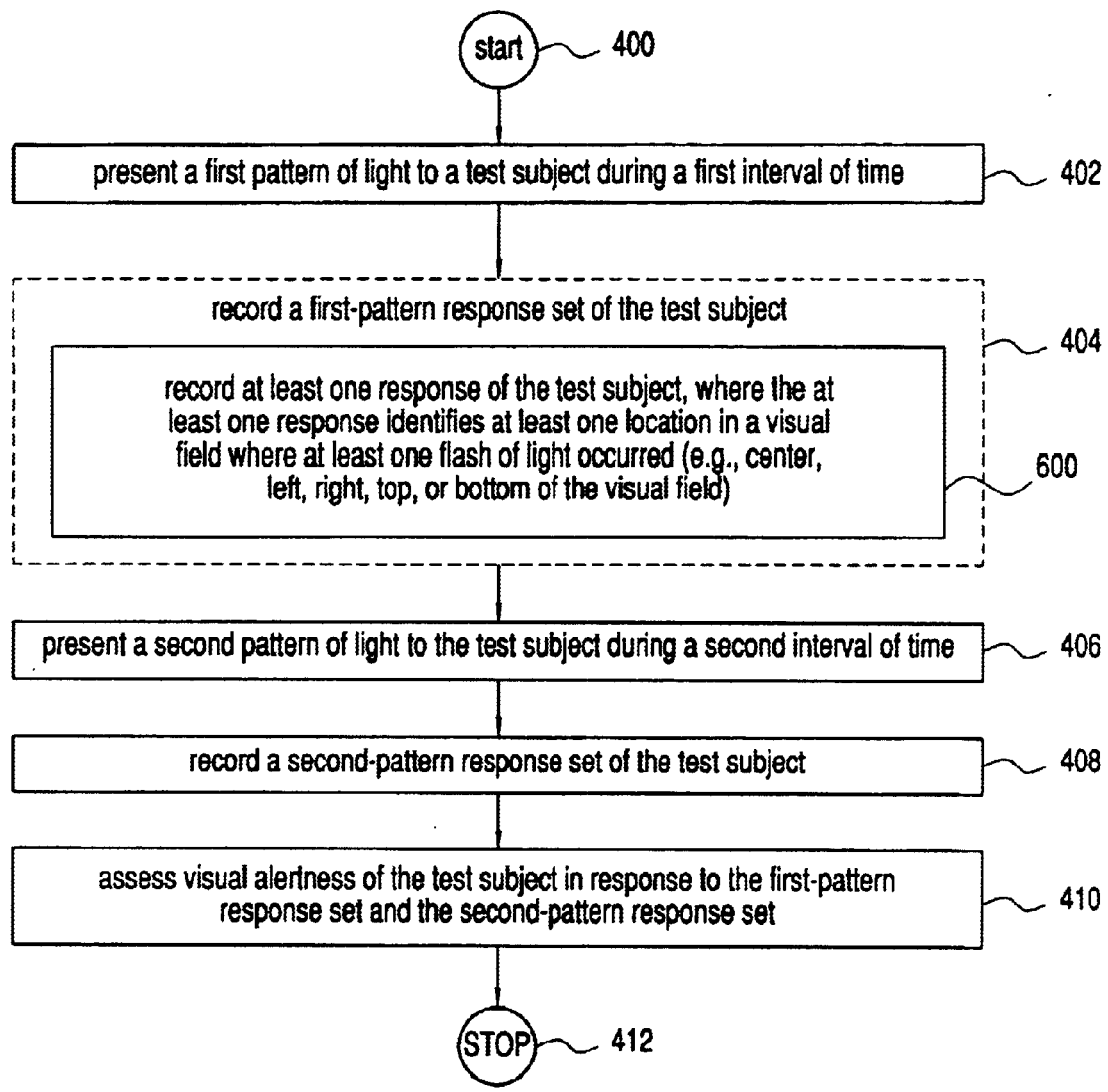

FIG. 6 depicts an alternate implementation of the process shown in FIG. 4.

Figure 7:
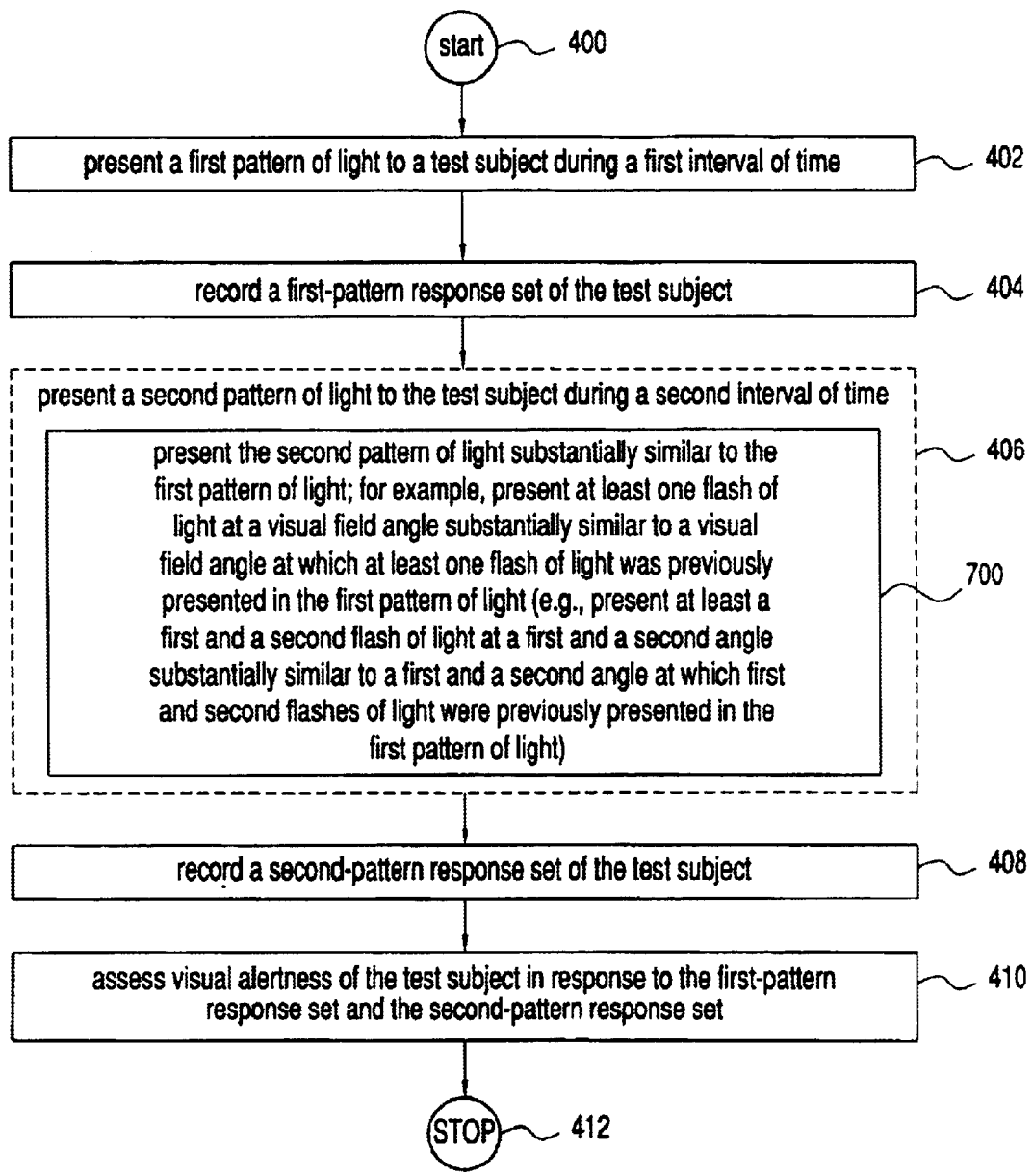

FIG. 7 shows an alternate implementation of the process depicted in FIG. 4.

Figure 8:
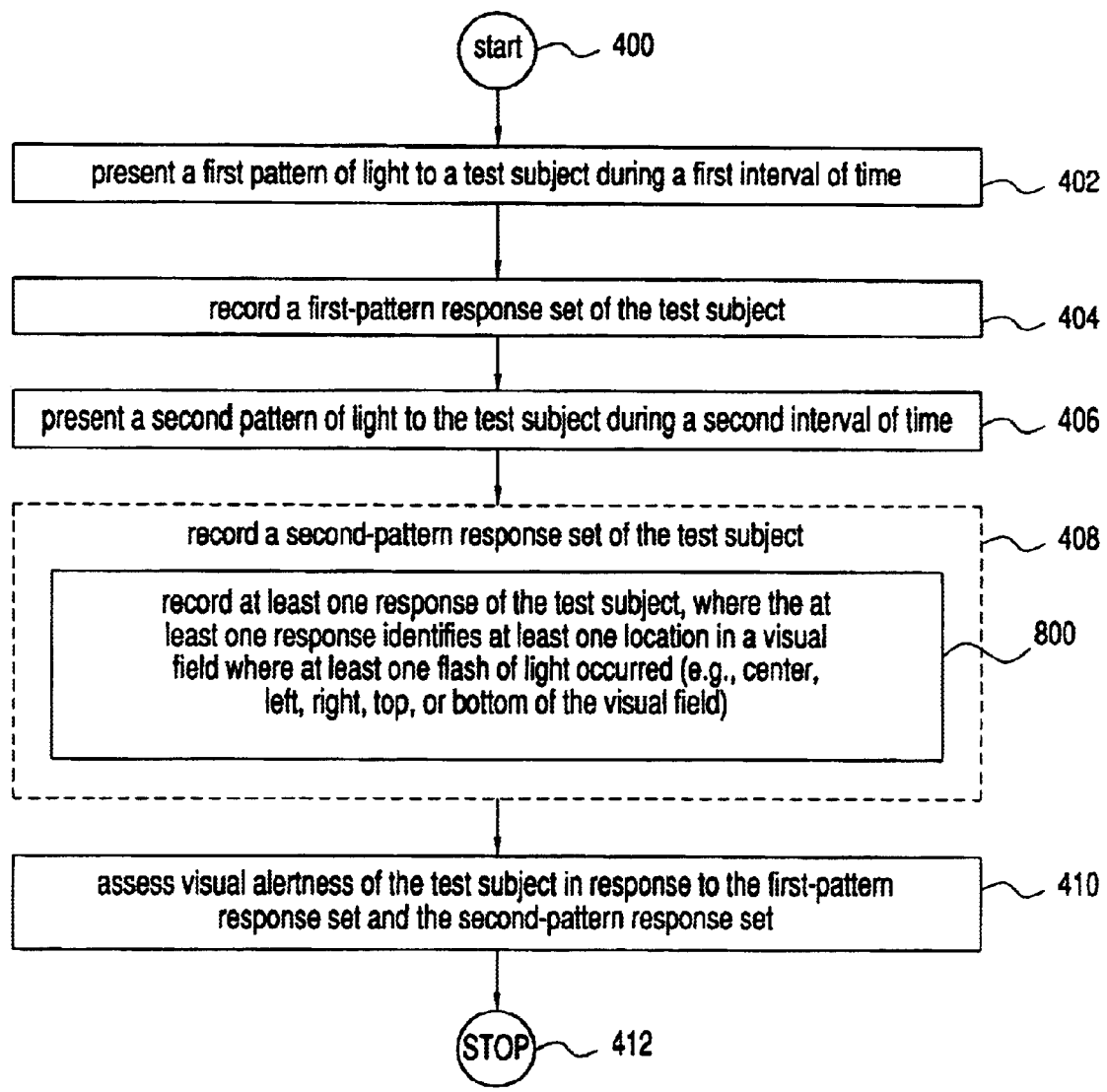

FIG. 8 depicts an alternate implementation of the process shown in FIG. 4.

Figure 9:
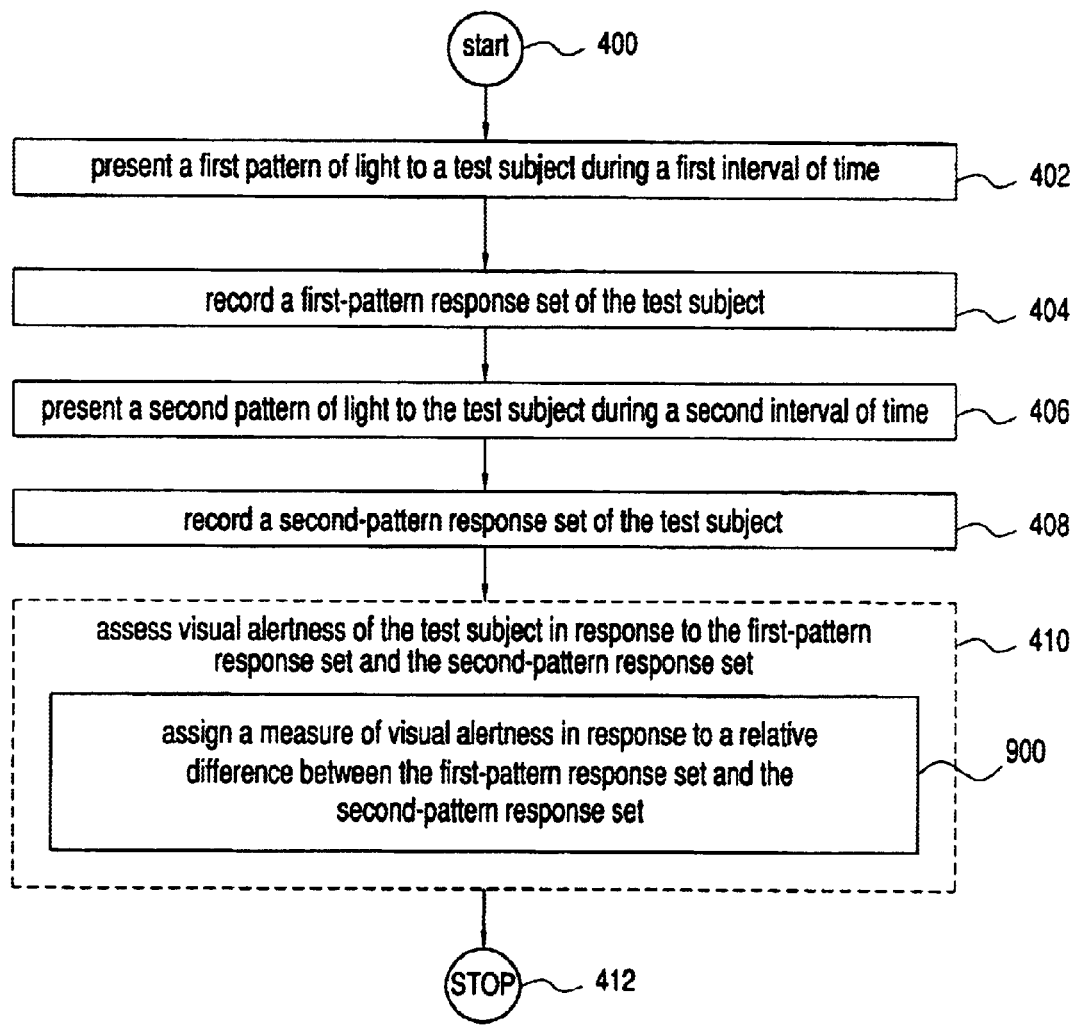

FIG. 9 illustrates an alternate implementation of the process shown in FIG. 4.

Figure 10:
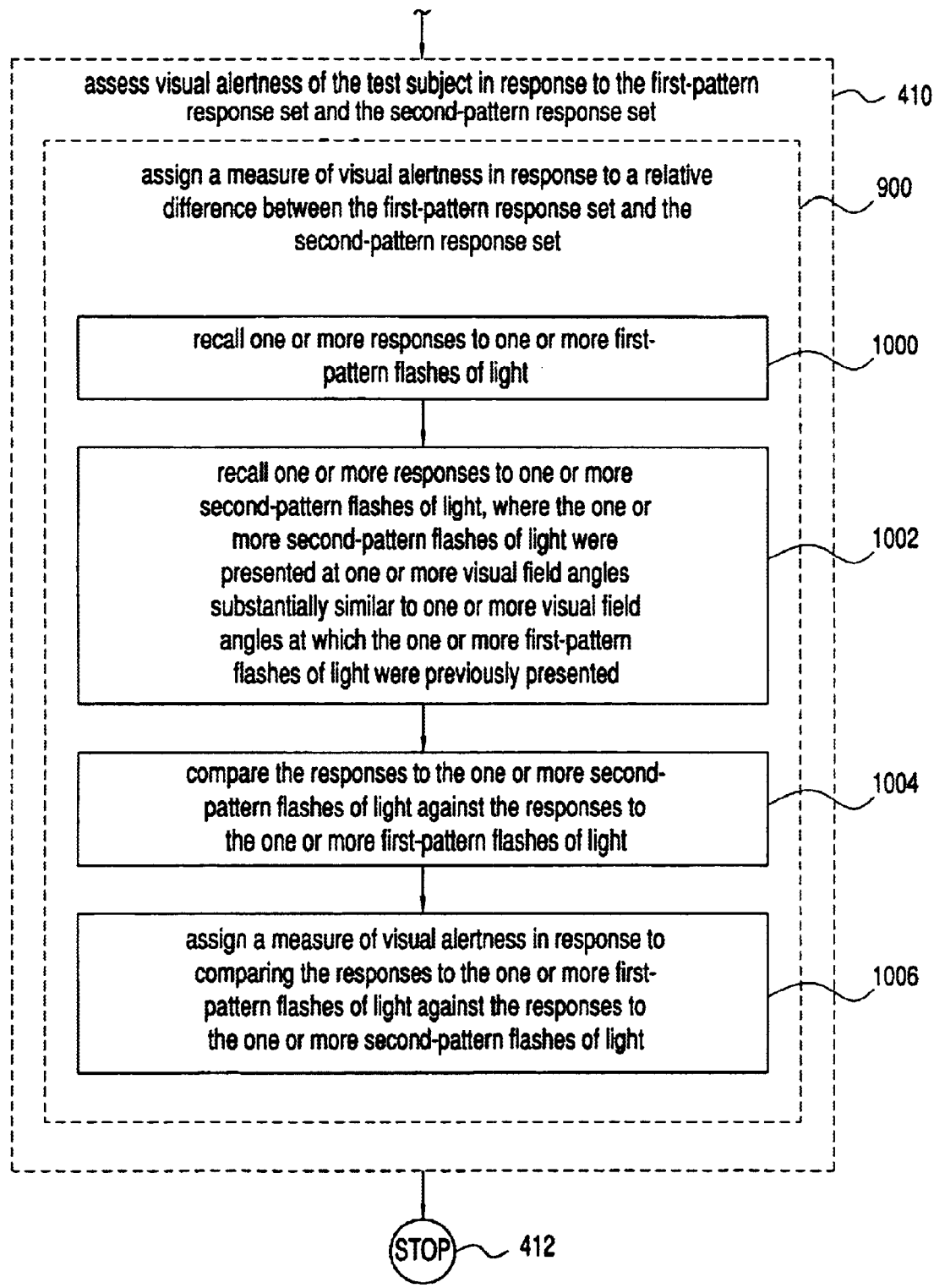

FIG. 10 shows an alternate implementation of the process shown in FIG. 9.

The use of the same symbols in different drawings typically indicates similar or identical items.

DETAILED DESCRIPTION OF THE INVENTION

The inventors have discovered that physical and/or mental impairment arising from sleep deprivation may be correlated with visual neglect. That is, the inventors have discovered that by detecting visual neglect, an inference as to physical and/or mental sleep-deprivation related impairment may be made.

Figure 1A:
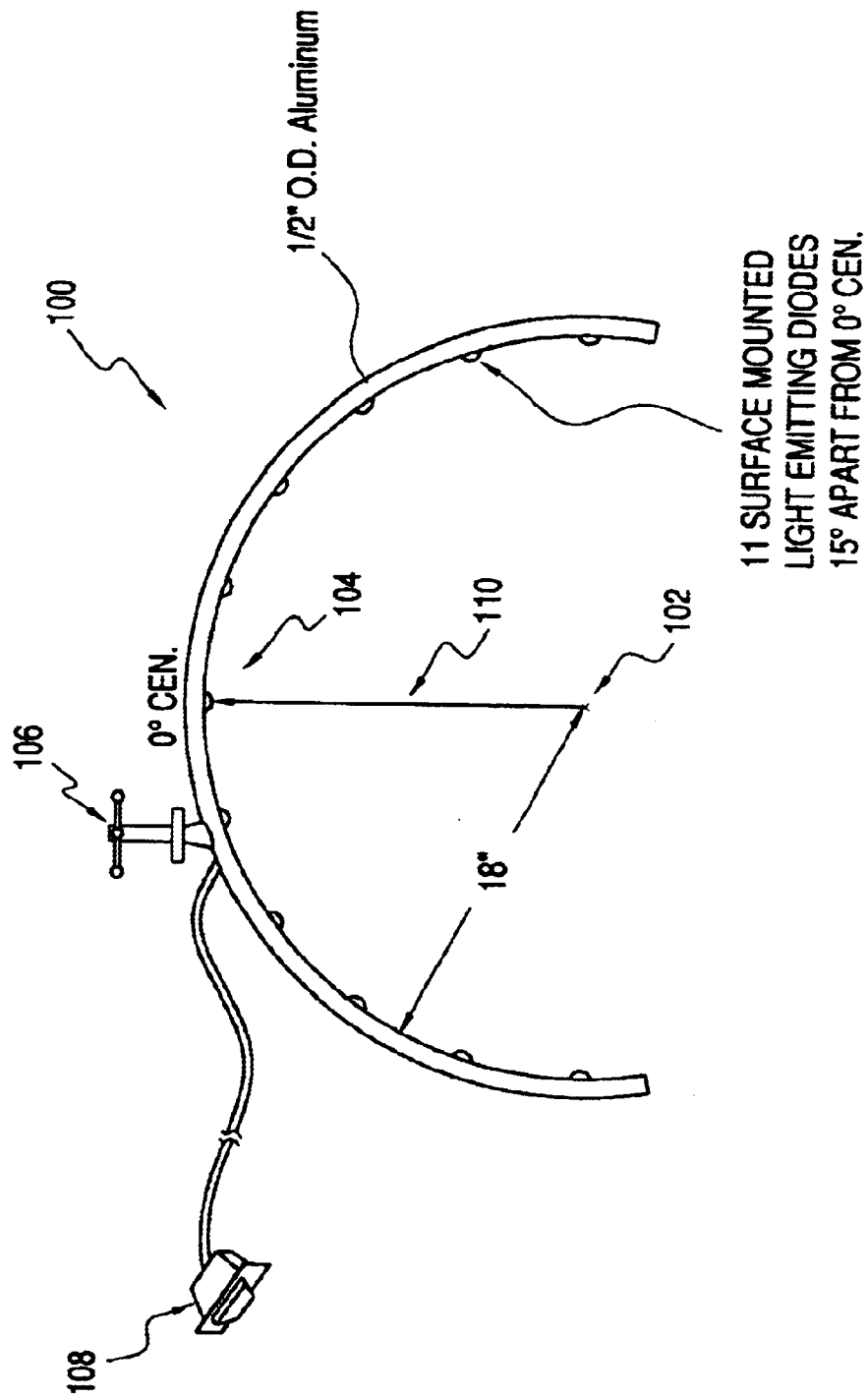
FIG. 1A shows a top-plan view of a lateral visual field tester (LVFT) device 100.

With reference to the figures, and in particular with reference now to FIG. 1A, shown is a top-plan view of a lateral visual field tester (LVFT) device 100, which in one implementation is a structure capable of statically supporting light emitting diodes, such as a metal, polymeric, or wooden structure. Depicted is that, in one implementation, eleven (11) surface-mount light emitting diodes (which serve as specific implementations of electric lamps, and which could just as easily be replaced with incandescent bulbs) have been positioned at 15-degree visual field angle intervals along the LVFT device 100, where the visual field angles are measured relative to a frame of reference defined by a line 110 extending between a predefined expected center position 102 of a test subject's head (not shown), when the test subject is positioned in predefined testing position (e.g., sitting in a correctly positioned testing chair), and a light emitting diode 104 located at the horizontal center of the LVFT device 100. Illustrated is that, in one implementation, the LVFT device 100 has a mounting clamp 106, which is typically used to affix the LVFT device 100 in a position within the work environment of a subject to be tested. For example, affixing the LVFT device 100 within an interior of a fixed-wing aircraft. Also shown is a 25-pin electrical connector 108, which in one limitation is used to allow a data processing system to interface and provide control to the light emitting diodes spaced along the LVFT device 100.

Figure 1B:
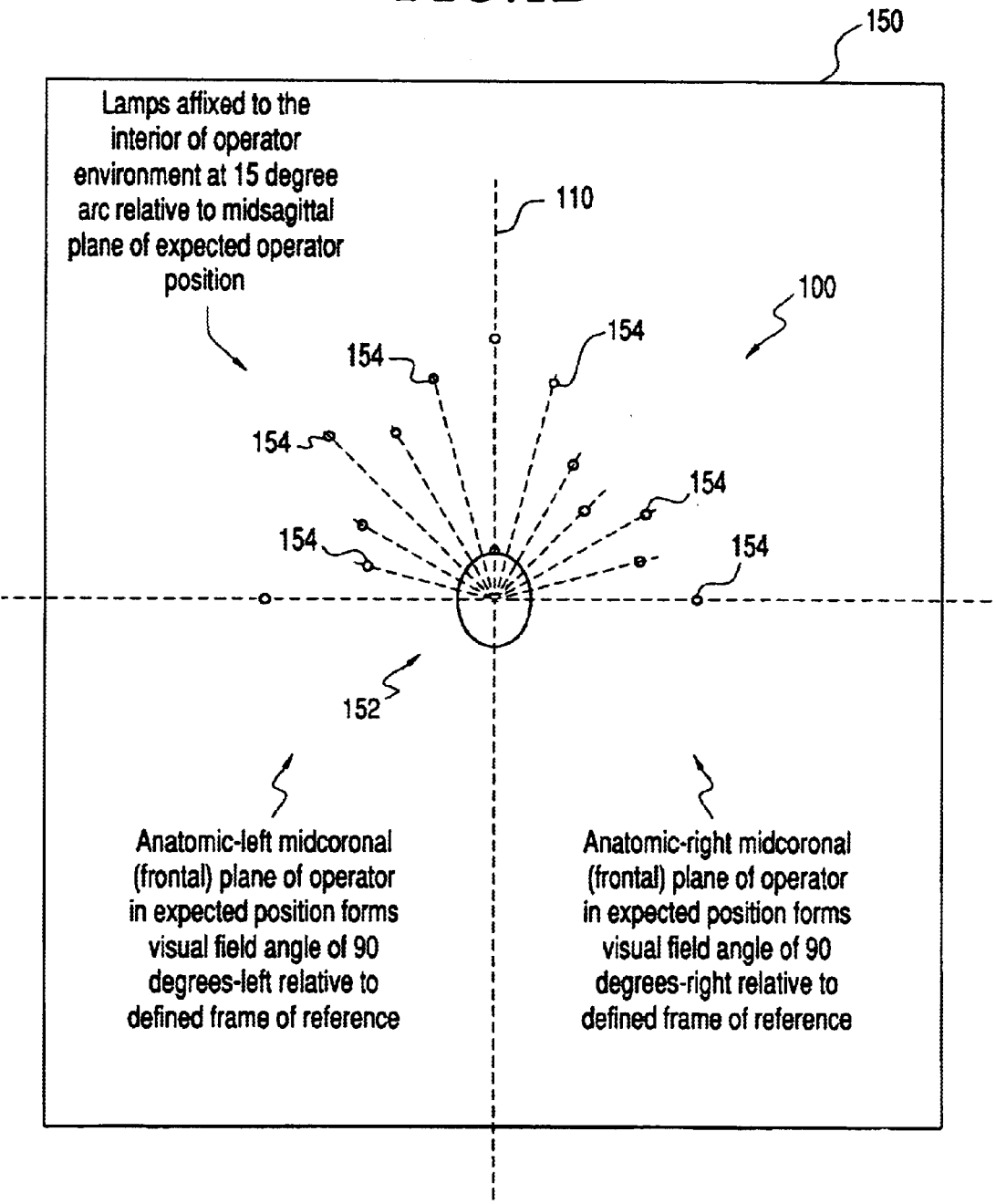
FIG. 1B depicts an alternate view of the way the visual field frame of reference is defined.

Referring now to FIG. 1B, depicted is an alternate view of the way the visual field frame of reference is defined. Illustrated is a top-plan view of an operator environment 150 of a human operated mechanism (e.g., a cockpit of an airplane, a cab of a tractor-trailer, a cabin of a locomotive, a bridge of a watercraft, a seat proximate to an air traffic controller terminal, or a position proximate to a piece of human-operated factory automation). Shown is a top-plan view of an expected human-operator head position 152, which in one implementation is a predefined location which is to substantially equate to where it is expected that a human operator's head will normally be positioned when operating the mechanism (e.g., the normal position of a pilot's head when the pilot is flying an airplane, the normal position of a driver's head when the driver is driving a tractor-trailer, the normal position of an engineer's head when the engineer is driving a locomotive, the normal position of a pilot's head when the pilot is piloting a watercraft, the normal position of an air traffic controller's head when the air traffic controller is operating an air traffic controller terminal, or the normal position of a worker's head when the worker is operating a piece of factory automation). Depicted is that LVFT device 100 has been constructed via thirteen (13) lamps 154, affixed within the operator environment 150, and spaced at 15-degree visual field angles, where the visual field angles are measured relative to a frame of reference defined by the top-plan view of the midsagittal plane (e.g., the line 110, which is what the midsagittal plane looks like in top-plan view) of the expected human operator's head position. An alternate way of describing the frame of reference used to define the visual field angles is that, that the LVFT device 100 has been constructed via eleven (11) lamps, affixed within the operator environment 150, spaced at 15-degree visual field angles, where the visual field angles are measured relative to a frame of reference defined such that the anatomic-left midcoronal (frontal) plane of a test subject's head would form a visual field angle of ninety (90) degrees-left relative to the frame of reference, while the anatomic-right midcoronal (frontal) plane of a test subject's head would form a visual field angle of ninety (90) degrees-right relative to the frame of reference. Further illustrated in FIG. 1B is that in some implementations the lamps vary in their distances from the expected human-operator head position 152. Although FIGS. 1A and 1B respectively describe eleven (11) lamps and thirteen (13) lamps spaced at 15 degree visual field angle intervals, it is to be understood that other numbers of lamps and other visual field angle intervals are contemplated, so long as that the lamps are placed from far peripheral positions to central positions through the visual field. In addition to the foregoing, the inventors point out that, in one implementation, the preferable position of the frontal plane would be at the midpoint of the eyes rather than the midpoint of the head, but that for sake of conceptual clarity they have herein described the visual field angles in relation to the midcoronal (frontal) plane, in that the location of the midcoronal (frontal) plane is well-known to those having ordinary skill in the art. The inventors also point out that, in actual conditions of operation, they do not expect the operator's head to remain static; rather, the operator positioning described herein is a baseline design parameter illustrating a frame of reference for the visual field angles.

Figure 2:
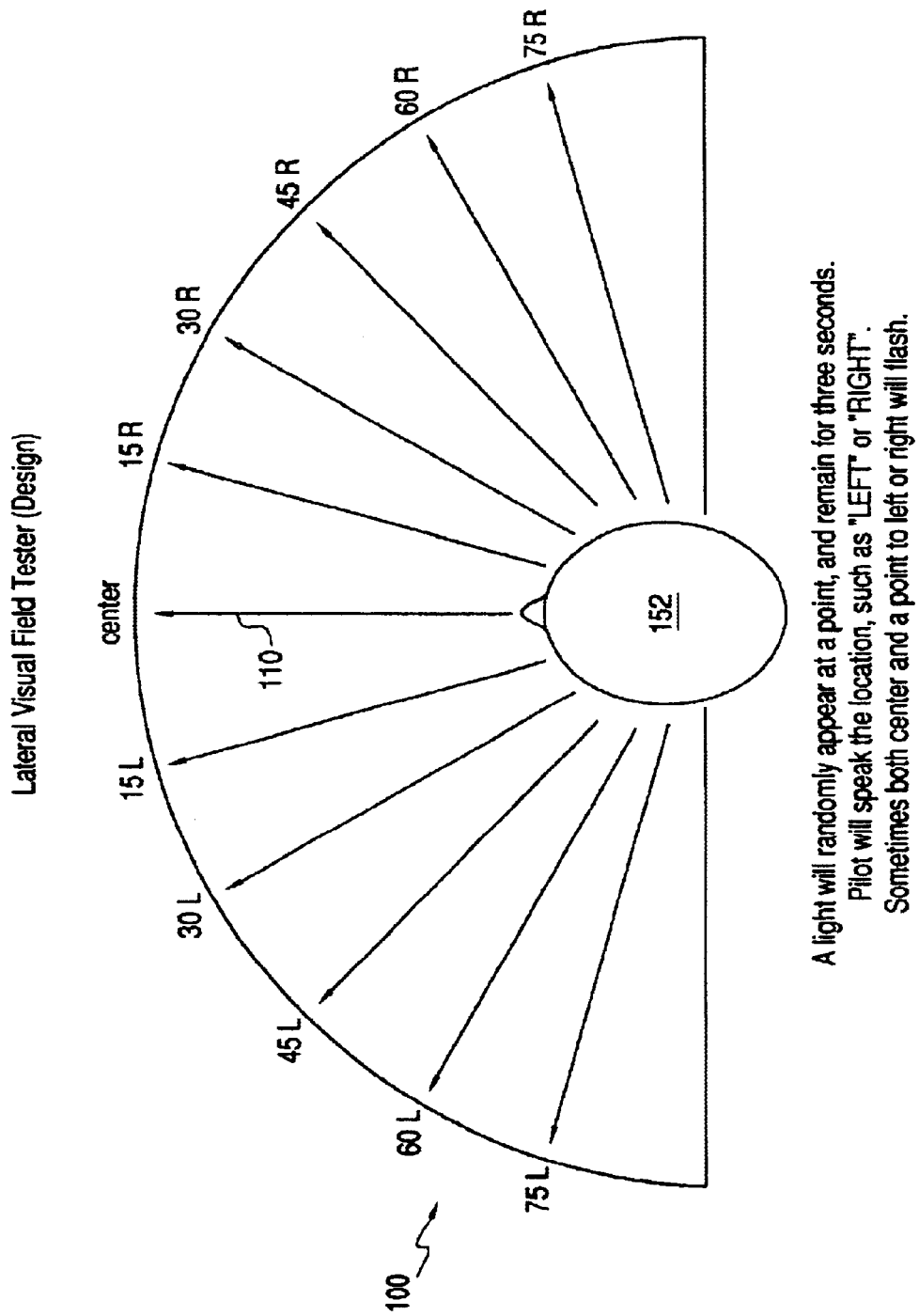
FIG. 2 depicts a top-plan view which illustrates preferable design features of the LVFT device 100.

Referring now to FIG. 2, depicted is a top-plan view which illustrates preferable design features of the LVFT device 100. Illustrated is that, in one implementation, it is preferable that lamps, such as the lamps (e.g., light emitting diodes) shown and described in relation to FIGS. 1A and 1B, are positioned such that they will be spaced at 15-degree visual field angle intervals, where the visual field angles are measured relative to a frame of reference defined by the midsaggital plane 110 of an expected position 152 of a test subject's head.

With reference now to FIG. 3, shown is a perspective view of an implementation of the LVFT device 100 in the context of a data processing system 300, audio-visual recording machinery 302, and an interface device 304. Depicted is that the LVFT device 100 is being utilized to administer a sleep deprivation impairment test to a human test subject 306. In one implementation, a computer program, running on data processing system 300, causes various of the light emitting diodes to flash at various visual field angles. In response, in one implementation, the human test subject 306 attempts to orally identify the position of each flash of light presented. The responses of the human test subject are recorded by audio-visual recording machinery 302.

A LVFT device 100 has been shown and described in relation to FIGS. 1A–3. However, other implementations of the LVFT device 100 are contemplated. Specifically, it is contemplated that for other LVFT devices, the light emitting diodes will be substantially directly affixed within the environments in which the LVFT devices will be utilized. For example, in one implementation, the light emitting diodes will be affixed upon surfaces interior to the cockpit of an airplane, where the light emitting diodes are affixed such that they are arranged in apattern substantially similar to their arrangement as shown and/or described in relation to FIG. 1A, 1B, 2, or 3. As another example, in one implementation, the light emitting diodes will be affixed upon surfaces interior to the cab of a tractor-trailer, where the light emitting diodes are affixed such that they are arranged in a pattern substantially similar to their arrangement as shown and/or described in relation to FIG. 1A, 1B, 2, or 3.

A LVFT device 100 has been shown and described, in relation to FIGS. 1A–3, as having a "half circle" shape. In other contemplated implementations, the LVFT device 100 has a half-oval shape. In other contemplated embodiments, the LVFT device 100 is formed via light emitting diodes arranged within the cockpit of an aircraft, or within the cab of a semi tractor-trailer, or within the cabin of a locomotive, or within the bridge of a watercraft, or upon the surface of an air traffic controller terminal, or upon the surface of human-operated factory automation. In such contemplated implementations, symmetry is to be maintained, but not necessarily a circular form. The inventors have found that as long as the arcs (e.g., visual field angles) between the stimuli supplied by the light emitting diodes is maintained, the distance of the stimuli from the eye may vary according to the operator environment constraints. For example, the distance of the lamps from the test subject may vary, such as was shown and described in relation to FIG. 1B, in response to constraints such as the size and shape of the operator environment (e.g., the cockpit of an aircraft, the cab of a semi tractor-trailer, the cabin of a locomotive, the bridge of a watercraft, the surface of an air traffic controller terminal, or the surface of human-operated factory automation).

Referring now to FIG. 4 and, FIGS. 1A–3, shown is a high-level logic flowchart depicting a process. Method step 400 depicts the start of the process. Method step 402 illustrates presenting a first pattern of light to a test subject during a first interval of time; for example, via a computer program executing on data processing system 300 activating various of the light emitting diodes of the LVFT device 100 in a first defined pattern during a first defined interval of time.

Method step 404 shows recording a first-pattern response set of the test subject; for example, in one implementation, the human test subject 306 attempts to orally identify the position of each flash of light presented in the first pattern of light, and the responses of the human test subject are recorded by audio-visual recording machinery 302.

Method step 406 depicts presenting a second pattern of light to the test subject during a second interval time; for example, via a computer program executing on data processing system 300 activating various of the light emitting diodes of the LVFT device 100 in a second defined pattern during a second defined interval of time.

Method step 408 illustrates recording a second-pattern response set of the test subject; for example, in one implementation, the human test subject 306 attempts to orally identify the position of each flash of light presented in the second pattern of light, and the responses of the human test subject are recorded by audio-visual recording machinery 302.

Method step 410 shows assessing visual alertness of the test subject in response to the first-pattern response set and the second-pattern response set; for example, in one implementation, via a computer program, executing on data processing system 300, comparing the first-pattern response set against the second-pattern response set, and assigning a measure of visual alertness based on how well the first-pattern response set and the second-pattern response set match up.

Method step 412 depicts the end of the process.

With reference now to FIG. 5 and FIGS. 1A–3, shown is an alternate implementation of the process depicted in FIG. 4. Depicted is that, in one implementation, method step 402—presenting a first pattern of light to the test subject during a first interval of time—includes method step 500. Method step 500 illustrates presenting at least one flash of light in a periphery of a visual field; for example, presenting at least a first flash of light at a first visual field angle, and presenting at least a second flash of light at a second visual field angle, where at least one of the first and second visual field angles is a nonzero angle. In one implementation of method step 500, at least one light emitting diode, in the LVFT device 100, located at a nonzero visual field angle, is activated. In another implementation of method step 500, two light emitting diodes, in the LVFT device 100, are activated, where at least one of the activated light emitting diodes is located at a nonzero visual field angle.

Referring now to FIG. 6 and FIGS. 1A–3, depicted is an alternate implementation of the process shown in FIG. 4. Illustrated is that, in one implementation, method step 404—recording a first-pattern response set of the test subject—includes method step 600. Method step 600 shows recording at least one response of the test subject, where the at least one response identifies at least one location in a visual field where at least one flash of light occurred (e.g., center, left, right, top, or bottom of the visual field—although only center, left, and right visual field angles are illustrated herein, those having ordinary skill in the art will recognize that the mechanisms and processes described herein may be extended to top and bottom visual field angles via a reasonable amount of experimentation); for example, if a light emitting diode at visual field angle of forty-five (45) degrees-left were activated, and the human test subject 306 noticed the light from the activated light emitting diode, the human test subject 306 would indicate that a light in the left of her visual field had been detected. In one implementation, the human test subject 306 indicates the location of the flash via an oral response (e.g., the patient stating "left") which is recorded by audiovisual recording equipment 302, while in another implementation the human test subject 306 indicates the location of the flash via a mechanical response (e.g., pressing a left-hand button on steering wheel, or depressing a left-foot pedal) which is recorded by a computer program executing on data processing system 300.

With reference now to FIG. 7 and FIGS. 1A–3, shown is an alternate implementation of the process depicted in FIG. 4. Depicted is that, in one implementation, method step 406—presenting a second pattern of light to the test subject during a second interval of time—includes method step 700. Method step 700 illustrates presenting the second pattern of light substantially similar to the first pattern of light; for example, presenting at least one flash of light at a visual field angle substantially similar to a visual field angle at which at least one flash of light was previously presented in the first pattern of light (e.g., presenting at least a first and a second flash of light at a first and a second angle substantially similar to a first and a second angle at which first and second flashes of light were previously presented in the first pattern of light). In one implementation of method step 700, at least one light emitting diode, in the LVFT device 100, located at a nonzero visual field angle utilized in the presentation of the first pattern of light, is activated. In another implementation of method step 700, two light emitting diodes, in the LVFT device 100, are activated, where at least one of the activated light emitting diodes is located at a nonzero visual field angle utilized in the presentation of the first pattern of light.

Referring now to FIG. 8 and FIGS. 1A–3, depicted is an alternate implementation of the process shown in FIG. 4. Illustrated is that, in one implementation, method step 408 recording a second-pattern response set of the test subject includes method step 800. Method step 800 shows recording at least one response of the test subject, where the at least one response identifies at least one location in a visual field where at least one flash of light occurred (e.g., center, left, right, top, or bottom of the visual field); for example, if a light emitting diode at visual field angle of forty-five (45) degrees-left were activated, and the human test subject 306 noticed the light from the activated light emitting diode, the human test subject 306 would indicate that a light in the left of her visual field had been detected. In one implementation, the human test subject 306 indicates the location of the flash via an oral response (e.g., the patient stating "left") which is recorded by audiovisual recording equipment 302, while in another implementation the human test subject indicates the location of the flash via a mechanical response (e.g., pressing a left-hand button on steering wheel, or depressing a left-foot pedal) which is recorded by a computer program executing on data processing system 300.

With reference now to FIG. 9, and FIGS. 1A–3, illustrated is an alternate implementation of the process shown in FIG. 4. Shown is that, in one implementation, method step 410—assessing visual alertness in response to the first-pattern response set and the second-pattern response set—includes method step 900. Method step 900 depicts assigning a measure of visual alertness in response to a relative difference between the first-pattern response set and the second-pattern response set.

Referring now to FIG. 10, and FIGS. 1A–3, shown is an alternate implementation of the process shown in FIG. 9. Depicted is that, in one implementation, method step 900—assigning a measure of visual alertness in response to a relative difference between the first-pattern response set and the second-pattern response set—includes method steps 1000–1006. Method step 1000 illustrates recalling one or more responses to one or more first-pattern flashes of light; for example, recalling the human test subject's 100 responses to first-pattern flashes of light in the periphery of the human test subject's 100 visual field (e.g., recalling the human test subject's 100 responses to the flashes of light respectively presented at a visual field angle of thirty (30) degrees-right, and forty-five (45) degrees-right, thirty (30) degrees-left, and fifteen (15) degrees-left).

Method step 1002 shows recalling one or more responses to one or more second-pattern flashes of light, where the one or more second-pattern flashes of light were presented at one or more visual field angles substantially similar to one or more visual field angles at which the one or more first-pattern flashes of light were previously presented; for example, building off the example given for method step 1000, recalling the human test subject's 100 response to second-pattern flashes of light in the periphery of the human test subject's 100 visual field (e.g., recalling the human test subject's 100 responses to the flashes of light respectively presented at visual field angles substantially similar to the first-pattern flashes of light visual field angles of thirty (30) degrees-right, forty-five (45) degrees-right, thirty (30) degree's-left and fifteen (15) degrees-left). Note that while the visual field angles of the second-pattern flashes of light are preferably substantially similar to the visual field angles of the first-pattern flashes of light, the order of presentation of the second-pattern flashes of light preferably varies from the order of presentation of the first-pattern flashes of light so that the test subject cannot anticipate the second-pattern flashes of light based with her experience with the first pattern flashes of light.

Method step 1004 depicts comparing the responses to the one or more second-pattern flashes of light against the responses to the one or more first-pattern flashes of light; for example, determining the statistical variation between the responses to the second-pattern flashes of light and the first-pattern flashes of light. More specifically, comparing recorded second-pattern and first-pattern responses to second-pattern and first-pattern flashes of light which were presented at substantially the same visual field angles. In one implementation, the comparing is done via a computer program running on data processing system 300, while in another implementation the comparing is done manually by a human tester via use of a listing of the second-pattern and first-pattern flashes of light, and the test subject's 306 second-pattern and first-pattern response sets. In one implementation, all responses in the second-pattern response set are compared against corresponding responses in the first-pattern response set.

Method step 1006 illustrates assigning a measure of visual alertness in response to the comparing of method step 1004. The inventors have found that when the responses of the second-pattern response set start to differ from the responses of the first-pattern response set by one-third (⅓) or more, it is likely that the test subject's 306 physical and/or mental capabilities are moderately impaired. The inventors have found that when the responses of the second-pattern response set start to differ from the responses of the first-pattern response set by two-thirds (⅔) or more, it is likely that the test subject's 306 physical and/or mental capabilities are substantially impaired. The inventors point out that more refined impairments may be determined, in light of the teachings herein, via a reasonable amount of experimentation well within the ambit of one having ordinary skill in the art.

With reference now to Table 1 and FIGS. 1A–3, depicted is a specific example of how first and second patterns of light illustrated and described in relation to the processes of FIGS. 4–10 may be constructed. During each visual field testing session of the test subject 306, each of the fifteen (15) visual stimulus combinations depicted in Table 1 will be presented a total of ten (10) times. Consequently, in one implementation, during each visual field testing session there will be a total of 150 visual stimuli, for 450 seconds (7.5 min. of total stimulus time per 20-minute visual field testing session). Interstimulus intervals (ISI) will vary from six (6) to ten (10) seconds (i.e., each visual stimulus presented for three (3) seconds, with a post stimulus interval ranging between three (3) and seven (7) seconds). As shown in Table 1, the fifteen (15) visual stimulus combinations are as follows (the light emitting diodes (LEDs) and angle referred to are in relation to those shown and described in relation to FIGS. 1A–3):

| | |
|---|---|
| Stimulus a | Activating a single LED at a visual field angle of zero degrees |
| Stimulus b | Simultaneously activating a first LED at a visual field angle at seventy-five (75) degrees-left and a second LED at a visual field angle of zero degrees |
| Stimulus c | Simultaneously activating a first LED at a visual field angle of seventy-five (75) degrees-right and a second LED at a visual field angle of zero degrees |
| Stimulus d | Simultaneously activating a first LED at a visual field angle of sixty (60) degrees-left and a second LED at a visual field angle of zero degrees |
| Stimulus e | Simultaneously activating a first LED at a visual field angle out of sixty (60) degrees-right and a second LED at a visual field angle of zero degrees |
| Stimulus f | Activating a LED at seventy-five (75) degrees-left |

-continued

| | |
|---|---|
| Stimulus g | Activating a LED at seventy-five (75) degrees-right |
| Stimulus h | Activating a LED at sixty (60) degrees-left |
| Stimulus i | Activating a LED at sixty (60) degrees-right |
| Stimulus j | Activating a LED at forty-five (45) degrees-left |
| Stimulus k | Activating a LED at forty-five (45) degrees-right |
| Stimulus l | Activating a LED at thirty (30) degrees-left |
| Stimulus m | Activating a LED at thirty (30) degrees-right |
| Stimulus n | Activating a LED at fifteen (15) degrees-left |
| Stimulus o | Activating a LED at fifteen (15) degrees-right |

In one implementation, in response to each stimulus, in order to demonstrate appreciation of the stimulus, the human test subject 306 will speak: "left," "right," "center-left," "center-right," or simply "center." For example, if the human test subject 306 detected a flash in the left half of the visual field (e.g., detected an activated LED at thirty (30) degrees-left), the human test subject would respond "left"; if the human test subject 306 detected a flash at the center and in the right half of the visual field (e.g., detected an activated LED at zero degrees and a substantially simultaneously activated LED at thirty (30) degrees-right), the human test subject 306 would respond "center, right"; and if the human test subject 306 detected a flash in the right half of the visual field (e.g., detected an activated LED at fifteen (15) degrees-right), the human test subject would respond "right." In one implementation, each 20-minute testing session will be digitally audio-video-taped to insure fidelity of the stimulus-response sequence.

In one implementation, the order, and timing, at which the stimulus combinations are presented to the human test subject 306 are varied between the first pattern and the second pattern. However, insofar as such patterns are based upon the presentation of the fifteen (15) foregoing-illustrated stimulus combinations, it is apparent that the first pattern and the second pattern will be substantially similar in that, in the aggregate, the same number and type of stimulus combinations will be presented across both patterns.

While Table 1 and FIGS. 1A–3 have depicted a specific example of how first and second patterns of light illustrated and described in relation to the processes of FIGS. 4–10 may be constructed, those having ordinary skill in the art will appreciate that the teachings herein are not limited to the specific example(s) described. For instance, in another implementation, with respect to presenting and recording a first pattern, that first pattern may be made of multiple iterations of presentations of patterns of lights, and then compared to a second pattern that is itself made of multiple iterations of presentations of patterns of lights. For example, in another implementation, the first and second intervals of time during which the first and second patterns are respectively presented may be made up of discontinuous sub-intervals (e.g., an interval could be an aggregation of 20, 40, and 90 minute intervals). In addition, as has been described, in one implementation a first pattern during a first interval contains 150 stimuli over a 20-minute period, and a second pattern during a second interval contains 150 stimuli over a 20-minute period. However, in other implementations, a first pattern during a first interval may consist of several of fixed-time sub-intervals (e.g., 20, 40, or 90 minute intervals), and several stimuli sub-patterns of light, where the sub-intervals and the sub-patterns may be different from each other, and where the presentation of the sub-patterns making up the first pattern may span several days. Similarly when the second pattern set is presented and recorded sometime later (e.g., after a period of sleep deprivation) that second pattern can be likewise so varied in accordance with the spirit of the teachings herein. In addition, those having ordinary skill in the art will appreciate that the patterns need not be used directly, as has been described herein, but that such patterns may instead be subjected to averaging, or other statistical techniques, and that such averaging or other statistical techniques are a design choice within the purview of the system designer.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which aspects of the processes and/or systems described herein can be effected (e.g., hardware, software, and/or firmware), and that the preferred vehicle will vary with the context in which the processes and/or systems are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or (Ti operation within such block diagrams, flowcharts, or examples can be implemented, individually and/or collectively, by a wide range of hardware, software, firmware, or virtually any combination thereof. In one embodiment, the present invention may be implemented via Application Specific Integrated Circuits (ASICs). However, those skilled in the art will recognize that the embodiments disclosed herein, in whole or in part, can be equivalently implemented in standard Integrated Circuits, as one or more computer programs running on one or more computers (e.g., as one or more programs running on one or more computer systems), as one or more programs running on one or more controllers (e.g., microcontrollers), as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure. In addition, those skilled in the art will appreciate that the mechanisms of the present invention are capable of being distributed as a program product in a variety of forms, and that an illustrative embodiment of the present invention applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into data processing systems. That is, the devices and/or processes described herein can be integrated into a data processing system via a reasonable amount of experimentation. FIG. 3 shows an example representation of a data processing system into which at least a part of the herein described devices and/or processes may be integrated with a reasonable amount of experimentation. Data processing system 300 may be implemented utilizing any suitable commercially available computer system.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

What is claimed is:

1. A method comprising:

presenting a first pattern of light during a first interval of time;

recording a first pattern response set including recording at least one response of a test subject, where the at least one response identifies at least one location in a visual field where at least one flash of light occurred;

presenting a second pattern of light during a second interval of time;

recording a second-pattern response set; and assessing visual alertness in response to the first-pattern response set and the second-pattern response set.

2. The method of claim 1, wherein said recording at least one response of a test subject, where the at least one response identifies at least one location in a visual field where at least one flash of light occurred comprises:

recording at least one response of a test subject, where the at least one response identifies at least the center, left, right, top, or bottom of the visual field.

3. A method comprising:

presenting a first pattern of light during a first interval of time;

recording a first-pattern response set;

presenting a second pattern of light during a second interval of time;

recording a second-pattern response set including recording at least one response of a test subject, where the at least one response identifies at least one location in a visual field where at least one flash of light occurred;

assessing visual alertness in response to the first-pattern response set and the second-pattern response set.

4. The method of claim 3, wherein said recording at least one response of a test subject, where the at least one response identifies at least one location in a visual field where at least one flash of light occurred comprises:

recording at least one response of a test subject, where the at least one response identifies at least the center, left, right, top, or bottom of the visual field.

5. A method comprising:
   presenting a first pattern of light during a first interval of time;
   recording a first-pattern response set;
   presenting a second pattern of light during a second interval of time;
   recording a second-pattern response set; and
   assessing visual alertness in response to the first-pattern response set and the second pattern response set;
   wherein said assessing visual alertness in response to the first-pattern response set and the second-pattern response set comprises;
   assigning a measure of visual alertness in response to a relative difference between the first-pattern response set and the second-pattern response set.

6. The method of claim 5, wherein the first pattern of light comprises:
   at least two sub-patterns of light.

7. The method of claim 5, wherein the first interval of time comprises:
   at least two subintervals of time.

8. The method of claim 5, wherein said presenting a first pattern of light during a first interval of time comprises:
   presenting at least one flash of light in a periphery of a visual field.

9. The method of claim 5, wherein said presenting at least one flash of light in a periphery of a visual field comprises:
   presenting at least a first flash of light at a first visual field angle; and
   presenting at least a second flash of light at a second visual field angle.

10. The method of claim 5, wherein said presenting at least one flash of light in a periphery of a visual field comprises:
    activating at least one electric lamp positioned in the periphery of the visual field.

11. The method of claim 5, wherein said activating at least one electric lamp positioned in the periphery of the visual field comprises:
    said activating an electric lamp affixed to a mechanical device in the periphery of the visual field.

12. The method of claim 5, wherein the second pattern of light comprises:
    at least two sub-patterns of light.

13. The method of claim 5, wherein the second interval of time comprises:
    at least two sub-intervals of time.

14. The method of claim 5, whereinsaid presenting a second pattern of light during a second interval of time comprises:
    presenting the second pattern of light substantially similar to the first pattern of light.

15. The method of claim 14, wherein said presenting the second pattern of light substantially similar to the first pattern of light comprises:
    presenting at least one flash of light at a visual field angle substantially similar to a visual field angle at which at least one flash of light was original in the first pattern of light.

16. The method of claim 15, wherein said presenting at least one flash of light at a visual field angle substantially similar to a visual field angle at which at least one flash of light was original in the first pattern of light comprises:
    presenting at least a first and a second flash of light at a first and a second angle substantially similar to a first and a second angle at which first and second flashes of light were original in the first pattern of light.

17. The method of claim 14, wherein said presenting the second pattern of light substantially similar to the first pattern of light comprises:
    activating at least one electric lamp positioned in the periphery of the visual field.

18. The method of claim 17, wherein said activating at least one electric lamp positioned in the periphery of the visual field comprises:
    activating at least one electric lamp affixed to a mechanical device in the periphery of the visual field.

19. The method of claim 5, wherein said assigning a measure of visual alertness in response to a relative difference between the first-pattern response set and the second-pattern response set comprises:
    recalling one or more responses to one or more first-pattern flashes of light;
    recalling one or more responses to one or more second-pattern flashes of light, where the one or more second-pattern flashes of light were presented at one or more visual field angles substantially similar to one or more visual field angles at which the one or more first-pattern flashes of light were original;
    comparing the responses to the one or more second-pattern flashes of light against the responses to the one or more first-pattern flashes of light; and
    assigning a measure of visual alertness in response to said comparing.

20. A system comprising:
    means for presenting a first pattern of light during a first interval of time;
    means for recording a first-Pattern response set including:
    means for recording at least one response of a test subject, where the at least one response identifies at least one location in a visual field where at least one flash of light occurred;
    means for presenting a second pattern of light during a second interval of time:
    means for recording a second-pattern response set: and
    means for assessing visual alertness in response to the first-pattern response set and the second-pattern response set.

21. The system of claim 20, wherein said means for recording at least one response of a test subject, where the at least one response identifies at least one location in a visual field where at least one flash of light occurred comprises:
    means for recording at least one response of a test subject, where the at least one response identifies at least the center, left, right, top, or bottom of the visual field.

22. A system comprising:
    means for presenting a first pattem of light during a first interval of time;
    means for recording a first-pattern response set including:
    means for presenting a second pattern of light during a second interval of time;
    means for recording a second-pattern response set;
    wherein said means for recording a second-pattern response set comprises:
    means for recording at least one response of a test subject, where the at least one response identifies at least one location in a visual field where at least one flash of light occurred; and means for assessing visual alertness in response to the first-pattern response set and the second-pattern response set.

23. The system of claim 22, wherein said means for recording at least one response of a test subject, where the at least one response identifies at least one location in a visual field where at least one flash of light occurred comprises:

means for recording at least one response of a test subject, where the at least one response identifies at least the center, left, right, top, or bottom of the visual field.

24. A system comprising:

means for presenting a first pattern of light during a first interval of time;

means for recording a first-pattern response set;

means for presenting a second pattern of light during a second interval of time;

means for recording a second-pattern response set; and means for assessing visual alertness in response to the first-patter response set and the second-pattern response set;

wherein said means for assessing visual alertness in response to the first-pattern response set and the second-pattern response set comprises:

means for assigning a measure of visual alertness in response to a relative difference between the first-pattern response set and the second-pattern response set.

25. The system of claim 24, wherein the first pattern of light comprises:

at least two sub-patterns of light.

26. The system of claim 24, wherein the first interval of time comprises:

at least two sub-intervals of time.

27. The system of claim 24, wherein said means for presenting a first pattern of light during a first interval of time comprises:

means for presenting at least one flash of light in a periphery of a visual field.

28. The system of claim 27, wherein said means for presenting at least one flash of light in a periphery of a visual field comprises:

means for presenting at least a first flash of light at a first visual field angle; and means for presenting at least a second flash of light at a second visual field angle.

29. The system of claim 27, wherein said means for presenting at least one flash of light in a periphery of a visual field comprises:

means for activating at least one electric lamp positioned in the periphery of the visual field.

30. The system of claim 29, wherein said means for activating at least one electric lamp positioned in the periphery of the visual field comprises:

said means for activating an electric lamp affixed to a mechanical device in the periphery of the visual field.

31. The system of claim 24, wherein the second pattern of light comprises:

at least two sub-patterns of light.

32. The system of claim 24, wherein the second interval of time comprises:

at least two sub-intervals of time.

33. The system of claim 24, wherein said means for presenting a second pattern of light during a second interval of time comprises:

means for presenting the second pattern of light substantially similar to the first pattern of light.

34. The system of claim 33, wherein said means for presenting the second pattern of light substantially similar to the first pattern of light comprises:

means for activating at least one electric lamp positioned in the periphery of the visual field.

35. The system of claim 34, wherein said means for activating at least one electric lamp positioned in the periphery of the visual field comprises:

means for activating at least one electric lamp affixed to a mechanical device in the periphery of the visual field.

36. The system of claim 33, wherein said means for presenting the second pattern of light substantially similar to the first pattern of light comprises:

means for presenting at least one flash of light at a visual field angle substantially similar to a visual field angle at which at least one flash of light was original in the first pattern of light.

37. The system of claim 36, wherein said means for presenting at least one flash of light at a visual field angle substantially similar to a visual field angle at which at least one flash of light was original in the first pattern of light comprises:

means for presenting at least a first and a second flash of light at a first and a second angle substantially similar to a first and a second angle at which first and second flashes of light were original in the first pattern of light.

38. The system of claim 24, wherein said means for assigning a measure of visual alertness in response to a relative difference between the first-pattern response set and the second-pattern response set comprises:

means for recalling one or more responses to one or more first-pattern flashes of light;

means for recalling one or more responses to one or more second-pattern flashes of light, where the one or more second-pattern flashes of light were presented at one or more visual field angles substantially similar to one or more visual field angles at which the one or more first-pattern flashes of light were original;

means for comparing the responses to the one or more second-pattern flashes of light against the responses to the one or more first-pattern flashes of light; and means for assigning a measure of visual alertness in response to said means for comparing.

39. An apparatus for assessing visual alertness comprising:

a display substrate;

a plurality of visually displayable members associated with said substrate;

said members positioned to be within the area of visual perception of a user;

a power source;

means for displaying at least one of said visually displayable members for a first predetermined length of time to generate a first pattern-response set of a user and for displaying at least one of said visually displayable members for a second predetermined length of time to generate a second pattern-response set of a user; and a data processing system configured to compare said first-pattern response set against said second-pattern response set for assigning a measure of visual alertness based on said comparison.

40. The apparatus of claim 39, wherein said display substrate is configured in the shape of a semi-circle or oval radially disposed about a predetermined position for a user.

41. The apparatus of claim 39, wherein the visually displayable members are disposed at about 15-degree visual field angle intervals along the substrate relative to a frame of reference defined by an expected center position of a user's head.

42. The apparatus of claim 41, wherein a visually displayable member is positioned at the horizontal center of the substrate relative to the expected position of a user's head.

43. The apparatus of claim 41, wherein the visually displayable members are disposed at non-uniform distances from the expected position of a user's head.

44. The apparatus of claim 39, wherein said substrate is configured to mimic an operator environment of a human operated mechanism.

45. The apparatus of claim 39, further comprising an audio-visual system for recording a user's responses for generating said first and second response-sets.

46. The apparatus of claim 39, further comprising means for generating a first pattern of light and a second pattern of light, wherein said first pattern of light is used to generate said first pattern-response set and said second pattern of light is used to generate said second pattern-response set.

* * * * *